United States Patent
Lv et al.

(10) Patent No.: US 10,406,194 B2
(45) Date of Patent: Sep. 10, 2019

(54) POWDER FORMULATION, METHOD FOR PREPARING THE SAME AND USE THEREOF

(71) Applicant: INFINITUS (CHINA) COMPANY LTD., Jiang Men, Guangdong (CN)

(72) Inventors: Fang Lv, Guangdong (CN); Hongwei Zhao, Guangdong (CN); Qingtao Tang, Guangdong (CN)

(73) Assignee: INFINITUS (CHINA) COMPANY LTD., Jiang Men, Guangdong (CN)

( * ) Notice: Subject to any disclaimer, the term of this patent is extended or adjusted under 35 U.S.C. 154(b) by 0 days.

(21) Appl. No.: 16/024,869

(22) Filed: Jul. 1, 2018

(65) Prior Publication Data

US 2019/0111098 A1 Apr. 18, 2019

(30) Foreign Application Priority Data

Oct. 17, 2017 (CN) .......................... 2017 1 0962922

(51) Int. Cl.

| | | |
|---|---|---|
| *A61K 36/79* | (2006.01) | |
| *A61K 31/733* | (2006.01) | |
| *A61K 36/77* | (2006.01) | |
| *A61K 36/725* | (2006.01) | |
| *A61K 36/815* | (2006.01) | |
| *A61K 36/64* | (2006.01) | |
| *A61K 36/52* | (2006.01) | |
| *A61K 31/185* | (2006.01) | |
| *A61K 36/54* | (2006.01) | |
| *A61K 9/00* | (2006.01) | |
| *A61P 15/10* | (2006.01) | |
| *A23L 33/105* | (2016.01) | |
| *B01D 61/02* | (2006.01) | |
| *A23P 10/40* | (2016.01) | |
| *A61K 9/14* | (2006.01) | |

(52) U.S. Cl.
CPC ............ *A61K 36/79* (2013.01); *A23L 33/105* (2016.08); *A23P 10/40* (2016.08); *A61K 9/0056* (2013.01); *A61K 9/14* (2013.01); *A61K 31/185* (2013.01); *A61K 31/733* (2013.01); *A61K 36/52* (2013.01); *A61K 36/54* (2013.01); *A61K 36/64* (2013.01); *A61K 36/725* (2013.01); *A61K 36/77* (2013.01); *A61K 36/815* (2013.01); *A61P 15/10* (2018.01); *B01D 61/025* (2013.01); *A23V 2002/00* (2013.01); *A61K 2236/331* (2013.01); *A61K 2236/51* (2013.01)

(58) Field of Classification Search
None
See application file for complete search history.

(56) References Cited

FOREIGN PATENT DOCUMENTS

| CN | 1383872 A | * 12/2002 |
|---|---|---|
| CN | 1718023 A | 1/2006 |
| CN | 101069715 A | 11/2007 |
| CN | 102787062 A | 11/2012 |
| CN | 102860550 A | 1/2013 |
| CN | 107048420 A | 8/2017 |

OTHER PUBLICATIONS

Taiwanese First Office Action dated Apr. 23, 2019.

* cited by examiner

*Primary Examiner* — Susan Hoffman
(74) *Attorney, Agent, or Firm* — Yue (Robert) Xu; Apex Attorneys at Law, LLP

(57) ABSTRACT

The present disclosure relates to health care products, disclosing a powder formulation made from inulin, ARILLUS *DIMOCARPUS LONGAN*, FRUCTUS *ZIZIPHUS JUJUBE*, FRUCTUS *LYCIUM BARBARUM*, RADIX *REHMANNIA GLUTINOSA* PRAEPARATA, SEMEN *JUGLANS REGIA*, HERBA *CISTANCHE TUBULOSA*, taurine, FRUCTUS *SCHISANDRA CHINENSIS* and CORTEX *CINNAMOMUM CASSIA*, and a simple method for preparing the powder which is suitable for large-scale production. The powder of the present disclosure promotes the growth of experimental animals, enhances the sperm motility of the animals, improves the duration and frequency of sexual response, and increases the level of sex hormones and sexual organ coefficient ratio. The powder has an obvious function of improving sexual capacity, therefore can be used to prepare the health care foods having function on improving sexual capacity.

6 Claims, No Drawings

POWDER FORMULATION, METHOD FOR PREPARING THE SAME AND USE THEREOF

CROSS REFERENCE TO RELATED APPLICATIONS

This application claims the priority of Chinese Patent Application No. 201710962922.4, filed on Oct. 17, 2017, and the disclosures of which are hereby incorporated by reference.

FIELD

The present disclosure relates to the field of health care products, specifically to a powder formulation and a method for preparing the same, especially to a health care powder formulation mainly made from natural Chinese herbal medicine and having a function of improving sexual capacity.

BACKGROUND

Yang deficiency physique is insufficiency of human body's yang qi. Qi is the most fundamental matter that forms human body and keeps life activities of human body. Insufficiency of yang qi leads to a series of symptoms, such as tiredness, intolerance of cold, cold limbs, pale lips, lack of qi, less speaking, drowsiness, fatigue, spermatorrhea, clear and watery leucorrhea, diarrhea, frequent micturition, decreased libido and so on. People with yang deficiency physique are intolerant to cold and their hands and feet are not warm, and they are easy to sweat; they like hot diet, and are lack of energy and sleep a lot.

People's living standard has increased significantly in recent years, and people's consumption concept and health concept have changed a lot. In order to avoid the adverse effects of unhealthy, people pay more and more attention to the use of nutraceuticals. Currently, the health care foods for improving sexual capacity are mainly supplements with vitamins and minerals and invigorating medical materials, and most of them are in the form of oral liquid. Oral liquid has disadvantages of inconvenience of carrying, poor stability and short storage time. Large doses of adjuvants such as starch and hydroxymethyl cellulose are often added to the tablet when the tablets are made, which causes a long disintegration time. At the same time, it is inconvenient for people who have dysphagia, such as old people and children. Moreover, invigorating medical materials are not convenient to decoct, carry and take.

SUMMARY

In view of above, in order to overcome the deficiencies of the conventional art, an object of the present disclosure is to provide a powder formulation and the method for preparing the same. In the present disclosure, the powder having a function of improving sexual capacity is mainly made from natural Chinese herbal medicine, therefore the powder has natural components without addition of excipients and is convenient to be taken.

In order to achieve the goal of the present disclosure, the following technical solutions are used in the present disclosure.

A powder formulation, which is made from inulin, ARILLUS *DIMOCARPUS LONGAN*, FRUCTUS *ZIZIPHUS JUJUBE*, FRUCTUS *LYCIUM BARBARUM*, RADIX *REHMANNIA GLUTINOSA* PRAEPARATA, SEMEN *JUGLANS REGIA*, HERBA *CISTANCHE TUBULOSA*, taurine, FRUCTUS *SCHISANDRA CHINENSIS* and CORTEX *CINNAMOMUM CASSIA* as the starting materials.

Therein, preferably, the mass ratio of inulin, ARILLUS *DIMOCARPUS LONGAN*, FRUCTUS *ZIZIPHUS JUJUBE*, FRUCTUS *LYCIUM BARBARUM*, RADIX *REHMANNIA GLUTINOSA* PRAEPARATA, SEMEN *JUGLANS REGIA*, HERBA *CISTANCHE TUBULOSA*, taurine, FRUCTUS *SCHISANDRA CHINENSIS* and CORTEX *CINNAMOMUM CASSIA* is (10~100):(1~10):(1~10):(1~10):(1~10):(1~10):(0.1~5):(0.1~10):(0.1~5):(0.1~5).

In some embodiments, the mass ratio of inulin, ARILLUS *DIMOCARPUS LONGAN*, FRUCTUS *ZIZIPHUS JUJUBE*, FRUCTUS *LYCIUM BARBARUM*, RADIX *REHMANNIA GLUTINOSA* PRAEPARATA, SEMEN *JUGLANS REGIA*, HERBA *CISTANCHE TUBULOSA*, taurine, FRUCTUS *SCHISANDRA CHINENSIS* and CORTEX *CINNAMOMUM CASSIA* is 10:3:3:2:2:2:1:0.3:0.5:0.5.

In some embodiments, the mass ratio of inulin, ARILLUS *DIMOCARPUS LONGAN*, FRUCTUS *ZIZIPHUS JUJUBE*, FRUCTUS *LYCIUM BARBARUM*, RADIX *REHMANNIA GLUTINOSA* PRAEPARATA, SEMEN *JUGLANS REGIA*, HERBA *CISTANCHE TUBULOSA*, taurine, FRUCTUS *SCHISANDRA CHINENSIS* and CORTEX *CINNAMOMUM CASSIA* is 50:2.5:5:2.5:6.25:3.75:0.75:0.25:2.5:2.5.

In some embodiments, the mass ratio of inulin, ARILLUS *DIMOCARPUS LONGAN*, FRUCTUS *ZIZIPHUS JUJUBE*, FRUCTUS *LYCIUM BARBARUM*, RADIX *REHMANNIA GLUTINOSA* PRAEPARATA, SEMEN *JUGLANS REGIA*, HERBA *CISTANCHE TUBULOSA*, taurine, FRUCTUS *SCHISANDRA CHINENSIS* and CORTEX *CINNAMOMUM CASSIA* is 20:2.5:1:4:1:4:1.5:5:1:0.1.

The present disclosure also provides a method for preparing the powder formulation, comprising: extracting ARILLUS *DIMOCARPUS LONGAN*, FRUCTUS *ZIZIPHUS JUJUBE*, FRUCTUS *LYCIUM BARBARUM*, RADIX *REHMANNIA GLUTINOSA* PRAEPARATA, SEMEN *JUGLANS REGIA*, HERBA *CISTANCHE TUBULOSA*, FRUCTUS *SCHISANDRA CHINENSIS* and CORTEX *CINNAMOMUM CASSIA* by adding water, concentrating the extract, adding inulin and taurine to the extract, drying the extract and pulverizing the dried extract.

Therein, the extraction by adding water is decoction extraction.

Further, the decoction extraction is preferably performed by extracting for 1 to 2 times, and in each time extracting for 0.5 to 3 hours by adding water 3 to 20 times the weight of the starting materials.

In some embodiments, the decoction extraction is performed by adding water which is 20 times the weight of the starting materials and extracting for 3 hours.

In some embodiments, the decoction extraction is performed by adding water which is 5 to 20 times the weight of the starting materials and extracting for 0.5 to 3 hours at the first time, and adding water which is 3 to 15 times the weight of the starting materials and extracting for 0.5 to 2 hours at the second time. In some embodiments, the decoction extraction is performed by adding water which is 15 times the weight of the starting materials and extracting for 2 hours at the first time, and adding water which is 10 times the weight of the starting materials and extracting for 1 hour at the second time. In other embodiments, the decoction extraction is performed by adding water which is 5 times the weight of the starting materials and extracting for 1 hour at the first time, and adding water which is 5 times the weight of the starting materials and extracting for 0.5 hour at the second time.

In the method of the present disclosure, all the extract is collected after water extraction and then concentrated. The concentrating is a concentrating in a high-temperature tank or a concentrating by reverse osmosis.

Further, in the method of the present disclosure, drying is carried out after the concentration. The drying is spray drying, freeze drying, belt drying, microwave drying or vacuum drying.

Preferably, in the method of the present disclosure, there is a step of pulverization after drying. The particle size after the pulverization is preferably controlled between 40 meshes and 80 meshes.

Granulation and Packaging.

In some embodiments, the powder formulation of the present disclosure and the control sample are administrated by intragastric gavage, and the effects of the powder formulation of the present disclosure on male rats are observed. The results show that the powder formulation of the present disclosure accelerates the growth of the experimental animals, increases the motility of animal sperms, improves the duration and frequency of sexual response, and increases the level of sex hormone and the sexual organ coefficient ratio.

Thus, the present disclosure provides an application of the powder in preparing health care food which has a function of improving sexual capacity.

It can be concluded from the technical solutions above that the present disclosure provides a powder formulation which is made from inulin, taurine, ARILLUS DIMOCARPUS LONGAN, FRUCTUS ZIZIPHUS JUJUBE, FRUCTUS LYCIUM BARBARUM, RADIX REHMANNIA GLUTINOSA PRAEPARATA, SEMEN JUGLANS REGIA, HERBA CISTANCHE TUBULOSA, FRUCTUS SCHISANDRA CHINENSIS and CORTEX CINNAMOMUM CASSIA. The starting materials of the powder are all from natural Chinese herbal medicine without addition of excipient. It is clean and has natural components, in line with people's pursuit of natural and health foods. In addition, dosage required for the powder is small; it can be taken orally or dissolved in water; it is soluble in cold water and melts in mouth; it has a good taste and can be absorbed quickly. The method for preparing the powder in the present disclosure is simple and suitable for large-scale production. Also, it is easy to be carried. The powder obtained has a good stability and long storage time. Experiments show that the powder formulation of the present disclosure promotes the growth of experimental animals, enhances the motility of sperm of the animals, improves duration and frequency of the sex reaction, and increases the level of sex hormones and sexual organ coefficient ratio. The powder formulation has obvious effects on improving sexual capacity, therefore can be used to prepare the health care foods having function on improving sexual capacity.

DETAILED DESCRIPTION

The present disclosure provides a powder formulation and a method for preparing the same. One of ordinary skill in the art can learn from the contents herein and improve the process parameters appropriately. In particular, it shall be noted that all the similar substitutions and modifications are apparent to one of ordinary skill in the art and are to be considered within the scope of the present invention. The method and product of the present invention have been described with preferred examples. It is apparent that one of the ordinary skill in the art can make change or modify the combination to the method and product of the present invention without departing from the spirit, scope and spirit of the invention, therefore realizing and applying the techniques of the present invention.

In order to understand the present disclosure further, the technical solutions in the embodiments of the present disclosure will be described clearly and completely herein in conjunction with the examples of the present disclosure. Apparently, the described examples are only a part of the examples of the present disclosure, rather than all examples. Based on the examples in the present disclosure, all of other examples, made by one of ordinary skill in the art without any creative efforts, fall into the protection scope of the present disclosure.

Without special illustration, all the reagents in the examples of the present disclosure are commercial products, which can be purchased on the market.

Example 1. The Powder Formulation of the Present Disclosure

Formulation:

| | |
|---|---|
| Inulin | 2000 g |
| ARILLUS DIMOCARPUS LONGAN | 100 g |
| FRUCTUS ZIZIPHUS JUJUBE | 200 g |
| FRUCTUS LYCIUM BARBARUM | 100 g |
| RADIX REHMANNIA GLUTINOSA PRAEPARATA | 250 g |
| SEMEN JUGLANS REGIA | 150 g |
| HERBA CISTANCHE TUBULOSA | 30 g |
| Taurine | 0 g |
| FRUCTUS SCHISANDRA CHINENSIS | 100 g |
| CORTEX CINNAMOMUM CASSIA | 100 g |

Method for Preparing

ARILLUS DIMOCARPUS LONGAN, FRUCTUS ZIZIPHUS JUJUBE, FRUCTUS LYCIUM BARBARUM, RADIX REHMANNIA GLUTINOSA PRAEPARATA, SEMEN JUGLANS REGIA, HERBA CISTANCHE TUBULOSA, FRUCTUS SCHISANDRA CHINENSIS and CORTEX CINNAMOMUM CASSIA were added to water which was 20 times the weight of the starting materials and extracted for 3 hours. The extract was concentrated and the concentration temperature was controlled between 95 and 100° C. Inulin and taurine were added and spray drying was carried out to give spray drying powders. The powders were pulverized to give the health care powder formulation.

Example 2. The Powder Formulation of the Present Disclosure

Formulation

| | |
|---|---|
| Inulin | 1000 g |
| ARILLUS DIMOCARPUS LONGAN | 300 g |
| FRUCTUS ZIZIPHUS JUJUBE | 300 g |
| FRUCTUS LYCIUM BARBARUM | 200 g |
| RADIX REHMANNIA GLUTINOSA PRAEPARATA | 200 g |
| SEMEN JUGLANS REGIA | 200 g |
| HERBA CISTANCHE TUBULOSA | 100 g |
| Taurine | 30 g |
| FRUCTUS SCHISANDRA CHINENSIS | 50 g |
| CORIEX CINNAMOMUM CASSIA | 50 g |

Method for Preparing

ARILLUS DIMOCARPUS LONGAN, FRUCTUS ZIZIPHUS JUJUBE, FRUCTUS LYCIUM BARBARUM, RADIX REHMANNIA GLUTINOSA PRAEPARATA,

SEMEN *JUGLANS REGIA*, HERBA *CISTANCHE TUBULOSA*, FRUCTUS *SCHISANDRA CHINENSIS* and CORTEX *CINNAMOMUM CASSIA* were decoction extracted with water twice. At the first time, water which was 15 times the weight of the starting materials was added and extracted for 2 hours. At the second time, water which was 10 times the weight of the starting materials was added and extracted for 1 hour. The two extracts were combined and concentrated. The concentration temperature was controlled between 95 and 100° C. Inulin and taurine were added and belt drying was carried out to give belt drying powders. The powders were pulverized to give the health care powder formulation.

Example 3. The Powder Formulation of the Present Disclosure

Formulation

| | |
|---|---|
| Inulin | 2000 g |
| ARILLUS DIMOCARPUS LONGAN | 250 g |
| FRUCTUS ZIZIPHUS JUJUBE | 100 g |
| FRUCTUS LYCIUM BARBARUM | 400 g |
| RADIX REHMANNIA GLUTINOSA PRAEPARATA | 100 g |
| SEMEN JUGLANS REGIA | 400 g |
| HERBA CISTANCHE TUBULOSA | 150 g |
| Taurine | 500 g |
| FRUCTUS SCHISANDRA CHINENSIS | 100 g |
| CORTEX CINNAMOMUM CASSIA | 10 g |

Method for Preparing

ARILLUS *DIMOCARPUS LONGAN*, FRUCTUS *ZIZIPHUS JUJUBE*, FRUCTUS *LYCIUM BARBARUM*, RADIX *REHMANNIA GLUTINOSA* PRAEPARATA, SEMEN *JUGLANS REGIA*, HERBA *CISTANCHE TUBULOSA*, FRUCTUS *SCHISANDRA CHINENSIS* and CORTEX *CINNAMOMUM CASSIA* were decoction extracted with water twice. At the first time, water which was 5 times the weight of the starting materials was added and extracted for 1 hour. At the second time, water which was 5 times the weight of the starting materials was added and extracted for 0.5 hour. The two extracts were combined and reverse osmosis concentration was carried out. The concentration temperature was less than 40° C. Inulin and taurine were added and freeze drying was carried out. The pre-cold temperature was −30° C. and the drying lasted for 3 to 4 hours. After drying, the temperature was risen quickly to 60° C. and maintained for 1 hour; and then the temperature was risen to 80° C. slowly and maintained for 10 to 12 hours to give freeze drying powders. The powders were pulverized to give the health care powder formulation.

Experimental Test 1. Sexual Capacity Test

1. Materials and Equipment

Test sample: the health care powder formulation of Example 2.

Experimental animals: SPF grade male rats, in the end of their adaptation period, have a body weight of 200±20 g. SD rats were preferred, 8 to 10 rats per group.

The rats were randomly divided into groups according to their weights, a normal control group, a positive control group, a low-dose group, a medium-dose group and a high-dose group of the test sample. After one-week adaptive feed, the rats were subjected to administration by intragastric gavage once a day for 4 continues weeks. The normal control group was administered with physiological saline of the equal volume.

The method for preparing the low-, medium- and high-dose groups of the test sample were shown hereinafter.

High-dose group of the test sample (test sample solution of 0.3 g/mL): 13.5 g of the test sample was accurately weighed and 45 mL of ultrapure water was added to give a 0.3 g/mL solution, that was the high-dose group of the test sample (1.5 g/kg, 0.5 mL/100 g), which was equal to 30 times of the human recommended amount.

Medium-dose group of the test sample (test sample solution of 0.1 g/mL): 15 mL solution of the high-dose group was taken, and 30 mL of ultrapure water was added to give a medium-dose group of the test sample (0.5 g/kg, 0.5 mL/100 g), which was equal to 10 times of the human recommended amount.

Low-dose group of the test sample (test sample solution of 0.05 g/mL): 15 mL solution of the medium-dose group was taken, and 15 mL of ultrapure water was added to give a low-dose group of the test sample (0.25 g/kg, 0.5 mL/100 g), which was equal to 5 times of the human recommended amount.

The method for preparing the positive control group is shown hereinafter.

100 g of *Eurycoma longifolia* powders were accurately weighed and put into a flask (500 mL), and deionized water was added. Extraction was performed for 3 times. In each extraction, 400 ml deionized water was added and extraction was performed for 2 hours. The extracts were combined and concentrated, and the concentration was adjusted to 0.4 g/mL (crude material/water). 6.625 mL of *Eurycoma longifolia* primary liquid (0.4 g/mL) was accurately measured mixed with ultrapure water to a final volume of 50 mL, giving a solution with a concentration of 0.053 g/mL, i.e., *Eurycoma longifolia* positive control group (31.8/3 mg/kg, 0.5 mL/100 g), which was equal to 5 times of the human recommended amount.

2. Experiment Methods 2.1 Body Weight Measurement of the Rats

Before the administration, the rats were weighed and randomly divided into groups. After administration, the rats were weighed at a fixed time every week, and the weight-changing curve was drawn after the experiment.

2.2 Test of Penile Erection Index (PEI Value) of Rats in Each Group

After 5-day adaptive feed, the rats were subjected to administration by intragastric gavage once daily for 4 continues weeks. The control group was administered with physiological saline of the equal volume. Sexual ethnology observation was performed twice each week on the animals of each group. After administration, the animals of each group were divided into 3 batches, 3 to 4 rats per cage. Female rats were left outside the cage as the induction, and the duration of penis erection was observed (stimulation time of penis erection: from the beginning of observation to the first time of the penis erection, a total of nine measurements were made. The first data was measured before administration and then twice a week thereafter for a total of four weeks). In addition, a camera was used to continuously record the times of grooming at pudenda, crawling back and the number of participating animals within 90 minutes, and the PEI value was calculated.

PEI=the total number of sex-related behavioral responses in each group of rats×number of rats in each group that have correlated behavioral responses/number of rats in each group.

2.3 Test of Testosterone Level in Serum

After 4-week continuous administration, 1.5 ml blood sample was taken from venous plexus of canthus, placed for 1 hour, and centrifuged for 30 minutes at 3000 rmp. The serums were taken and testosterone level in serum was detected by an ELISA kit.

2.4 Test of Sperm Motility and Sexual Organ Coefficient Ratio

1% sodium pentobarbital (0.2 mL/100 g) was used in abdominal anesthesia. The rat was incised in the middle of hypogastrium and the testis was taken out. The testis and the epididymis were isolated and weighed. Thereafter, the epididymis was separated by a pair of ophthalmic scissors and cut in the middle. The tail part of the epididymis was taken out and placed in 2 mL of PBS (37° C., pre-warmed), cut into 3 pieces by a pair of ophthalmic scissors, incubated for 10 minutes. After the sperms in the epididymis were fully released, counting was performed under a microscope to calculate the sperm motility:

Sperm motility=(total number of sperms in the counting chamber−total number of the sperms which cannot move forward)÷total number of sperms in the counting chamber Finally, euthanasia was performed on the animals. The seminal vesicle and the levator ani muscle were taken and all the organs were weighed to calculate the organ coefficient of the organs was calculated.

2.4 Results

2.4.1 Weight Gaining Curve

After 3-week administration, weight gain of the rats in low-dose group was slightly lower than that of the normal control group. Weight of the rats in medium-dose group increased significantly, and the body weight reached 339.4±16.9 g after the fourth week, showing a weight increase of 119.8%, which was significantly higher than that of the normal group (329.8±21.7 g with a weight increase of 93.8%) and the *Eurycoma longifolia* group. There was little difference in other groups compared with the normal control group.

TABLE 1

Weight change of the rats

| Group | Week 0 | 1 | 2 | 3 | 4 |
|---|---|---|---|---|---|
| Normal Control Group | 170.2 ± 12.0 | 239.0 ± 12.4 | 286.9 ± 16.9 | 307.9 ± 12.6 | 329.8 ± 21.7 |
| Positive Control Group | 179.4 ± 6.7 | 234.7 ± 9.7 | 280.1 ± 12.9 | 310.2 ± 15.9 | 332.4 ± 18.7 |
| Low-Dose Group | 180.0 ± 2.4 | 250.5 ± 10.5 | 289.0 ± 14.9 | 301.6 ± 19.5 | 322.3 ± 20.8 |
| Medium-Dose Group | 154.4 ± 10.3 | 225.3 ± 14.2 | 278.9 ± 11.9 | 322.6 ± 13.0 | 339.4 ± 16.9 |
| High-Dose Group | 165.1 ± 10.8 | 227.1 ± 20.0 | 269.5 ± 20.5 | 302.4 ± 20.9 | 323.3 ± 21.9 |

TABLE 2

Effects of test sample on growth rate of rat body weight

| Group | Week 1 | 2 | 3 | 4 |
|---|---|---|---|---|
| Normal Control Group | 40.4 ± 7.3 | 68.5 ± 9.9 | 80.9 ± 7.4 | 93.8 ± 2.7 |
| Positive Control Group | 30.8 ± 5.4 | 56.2 ± 7.2 | 72.9 ± 8.8 | 85.3 ± 10.4 |
| Low-Dose Group | 39.2 ± 5.8 | 60.6 ± 8.3 | 67.5 ± 10.8 | 79.1 ± 11.5* |
| Medium-Dose Group | 45.9 ± 9.2 | 80.6 ± 7.7 | 108.9 ± 8.4** | 119.8 ± 10.9**## |
| High-Dose Group | 37.5 ± 12.1 | 63.2 ± 12.4 | 83.2 ± 12.6 | 95.8 ± 13.3 |

Comment: *$P < 0.05$, **$P < 0.01$, compared with the normal control group; #$P < 0.05$, ##$P < 0.01$, compared with the positive control group.

2.4.2 Sexual Organ Coefficient Ratio

After administration, testis, epididymis, levator ani muscle and seminal vesicle of rats in each group were taken and weighed, and sexual organ coefficient ratio of each group was compared. The results were shown in Table 3.

TABLE 3

Weight of animal organs in each group and sexual organ coefficient ratio (multiples of the normal control group)

| Organ | Normal Control Group | Eurycoma longifolia Group | Low-Dose Group | Medium-Dose Group | High-Dose Group |
|---|---|---|---|---|---|
| Testis | 1 | 1.02 ± 0.12 | 1.10 ± 0.09 | 1.02 ± 0.18 | 1.07 ± 0.2 |
| Epididymis | 1 | 1.14 ± 0.29 | 1.20 ± 0.27* | 1.18 ± 0.25* | 1.24 ± 0.18**# |

TABLE 3-continued

Weight of animal organs in each group and sexual organ coefficient ratio
(multiples of the normal control group)

| | Group | | | | |
|---|---|---|---|---|---|
| Organ | Normal Control Group | Eurycoma longifolia Group | Low-Dose Group | Medium-Dose Group | High-Dose Group |
| Levator Ani Muscle | 1 | 1.12 ± 0.24* | 1.11 ± 0.36* | 1.10 ± 0.26* | 1.22 ± 0.38* |
| Seminal Vesicle | 1 | 1.35 ± 0.39** | 1.28 ± 0.33* | 1.32 ± 0.41* | 1.46 ± 0.38** |

Comment: $\bar{x} \pm s$, n = 8; *P < 0.05, **P < 0.01, compared with the normal control group; #P < 0.05, compared with the positive group.

The results showed that except for sexual organ coefficient ratio of testis, the sexual organ coefficient ratio of the positive control group and the treatment groups of the test sample increased, wherein increase of the seminal vesicle was the most obvious. Effects of medium- and high-dose group of the test same were equal to that of the positive control group.

2.4.2 PEI Value of Rats

After administration, the duration and strength of sexual response, for example crawling back, grooming at pudendum and penis erection, in *Eurycoma longifolia* group and test sample groups increased. As shown in Table 4, average PEI value of *Eurycoma longifolia* group was significantly higher than that of the normal control group. All the PEI values of the low-, medium- and high-dose group of the test sample were higher than that of normal control group. Comparing with normal control group, there were significantly statistical differences, but there was no statistical difference when comparing with *Eurycoma longifolia* group.

TABLE 4

Average PEI value of rats in each group

| Number | Normal Control Group | Positive Control Group | Low-Dose Group | Medium-Dose Group | High-Dose Group |
|---|---|---|---|---|---|
| 1 | 119 | 228 | 215 | 135 | 135 |
| 2 | 148 | 217 | 280 | 202 | 198 |
| 3 | 96 | 181 | 115 | 182 | 188 |
| 4 | 156 | 218 | 148 | 224 | 162 |
| 5 | 89 | 340 | 174 | 219 | 176 |
| 6 | 257 | 199 | 199 | 208 | 184 |
| 7 | 109 | 155 | 133 | 205 | 301 |
| 8 | 128 | 335 | 440 | 146 | 181 |
| 9 | 137 | 196 | 243 | 146 | 143 |
| Mean Value | 137.7 ± 50.1 | 229.9 ± 64.8** | 216.3 ± 99.2* | 185.2 ± 34.4* | 185.3 ± 48.1* |

Comment; $\bar{x} \pm s$, n = 8; *P < 0.05, ***P < 0.01, compared with the normal control group. 2.4.3 Latency of penis erection 2-week after administration, latency of penis erection of the *Eurycoma longifolia* group and test sample groups was shortened comparing with that before administration (Table 5), and some test sample groups showed better effect than that of the positive control group. The medium-dose group performed particularly well.

TABLE 5

Changes of latency of penis erection of rats in each group after administration

| | Time | | | | | | | | |
|---|---|---|---|---|---|---|---|---|---|
| Group | 1 | 2 | 3 | 4 | 5 | 6 | 7 | 8 | 9 |
| Normal Control Group | 6.13 ± 2.94 | 7.25 ± 5.36 | 5.15 ± 2.51 | 5.27 ± 1.76 | 5.3 ± 2.13 | 4.7 ± 2.64 | 5.24 ± 2.00 | 5.45 ± 3.03 | 5.09 ± 1.21 |
| Positive Control Group | 6.8 ± 3.31 | 3.73 ± 3.49 | 1.55 ± 0.86* | 2.02 ± 1.24** | 1.08 ± 0.37** | 1.97 ± 0.99* | 1.45 ± 0.62** | 1.05 ± 0.45** | 1.15 ± 0.52** |
| Low-Dose Group | 3.91 ± 2.83 | 1.41 ± 0.81* | 1.97 ± 1.04* | 1.68 ± 0.62*** | 1.7 ± 0.57*** | 2.28 ± 1.22* | 2.2 ± 1.3*** | 1.11 ± 0.27*** | 1.85 ± 1.07*** |
| Medium-Dose Group | 6.91 ± 2.23 | 2 ± 0.50* | 1.3 ± 0.85** | 2.44 ± 1.78** | 3 ± 1.96* | 2.03 ± 1.28** | 1.84 ± 0.71*** | 1.25 ± 0.63** | 1.69 ± 0.96*** |

TABLE 5-continued

Changes of latency of penis erection of rats in each group after administration

| Group | Time | | | | | | | | |
|---|---|---|---|---|---|---|---|---|---|
| | 1 | 2 | 3 | 4 | 5 | 6 | 7 | 8 | 9 |
| High-Dose Group | 8.11 ± 3.28 | 3.31 ± 1.92 | 1.61 ± 0.94** | 2.05 ± 0.84*** | 2.78 ± 1.38** | 1.78 ± 0.92** | 1.81 ± 0.79*** | 2.11 ± 1.1* | 1.56 ± 1.5*** |

Comment:
*p < 0.05,
**p < 0.01,
***p < 0.001, compared with normal control group,.

2.4.4 Results of Testosterone in Serum

Results of test of testosterone in serum (Table 6) showed that the low-, medium- and high-dose groups of the test sample increased testosterone level in serum, wherein the increase of the low- and medium-dose groups were higher than that of the *Eurycoma longifolia* group.

TABLE 6

Comparison of testosterone level in serum

| Normal Control Group | 1 | 1 | 1 | 1 | 1 | 1 | 1 | 1 | Mean Value |
|---|---|---|---|---|---|---|---|---|---|
| Positive Control Group | 1.08 | 1.09 | 0.94 | 1.00 | 0.99 | 1.00 | 1.05 | 1.21 | 1.05 ± 0.08* |
| Low-Dose Group | 1.26 | 1.19 | 1.07 | 1.09 | 1.10 | 1.07 | 1.24 | 1.09 | 1.14 ± 0.08**# |
| Medium-Dose Group | 1.23 | 1.17 | 1.02 | 1.09 | 1.11 | 0.92 | 1.26 | 1.12 | 1.11 ± 0.11**# |
| High-Dose Group | 1.12 | 1.06 | 0.92 | 1.05 | 1.09 | 0.96 | 1.09 | 1.02 | 1.04 ± 0.07* |

Comment: the value of the normal control group is set as baseline 1 and others are the ratios to the normal control group;
$\bar{x} \pm s$, n = 8;
*P < 0.05,
**P < 0.01, compared with the normal control group;
P < 0.05, compared with the positive control group.

2.4.5 Results of Sperm Motility Test

Results of sperm motility test were shown in Table 7. The low-, medium- and high-dose groups of the test sample increased sperm motility of the male rats in a dose-dependent manner, wherein effect of the high-dose group equal to that of the positive control group.

TABLE 7

Motility of sperm of rats in each group

| Group | Sperm Motility (%) |
|---|---|
| Normal Control Group | 43.1 ± 11.3 |
| Positive Control Group | 69.3 ± 12.4*** |
| Low-Dose Group | 53.3 ± 4.1*## |
| Medium-Dose Group | 57.1 ± 8.9**# |
| High-Dose Group | 73.4 ± 10.3*** |

Comment: $\bar{x} \pm s$, n = 8; *P < 0.05, P < 0.01, *P < 0.001, compared with the normal control group; #P < 0.05, ##P < 0.01, compared with the positive control group.

The powder formulations obtained in Example 1 and Example 3 were subjected to above tests and showed similar effects as that of Example 2.

In view of above, the powder formulation of the present disclosure promotes the growth of experimental animals, increases the sperm motility of the animals, improves duration and frequency of sexual response, and increases sex hormone levels and sexual organ coefficient ratio. The effects are similar to that of the positive control drug, indicating that it has a good effect on improving sexual capacity.

The invention claimed is:

1. A method of improving sexual capacity, comprising administering a powder formulation to a subject in need thereof, wherein the powder formulation is made from inulin, ARILLUS *DIMOCARPUS LONGAN*, FRUCTUS *ZIZIPHUS JUJUBE*, FRUCTUS *LYCIUM BARBARUM*, RADIX *REHMANNIA GLUTINOSA* PRAEPARATA, SEMEN *JUGLANS REGIA*, HERBA *CISTANCHE TUBULOSA*, taurine, FRUCTUS *SCHISANDRA CHINENSIS* and CORTEX *CINNAMOMUM CASSIA* as the starting materials.

2. The method according to claim 1, wherein the mass ratio of inulin, ARILLUS *DIMOCARPUS LONGAN*, FRUCTUS *ZIZIPHUS JUJUBE*, FRUCTUS *LYCIUM BARBARUM*, RADIX *REHMANNIA GLUTINOSA* PRAEPARATA, SEMEN *JUGLANS REGIA*, HERBA *CISTANCHE TUBULOSA*, taurine, FRUCTUS *SCHISANDRA CHINENSIS* and CORTEX *CINNAMOMUM CASSIA* is (10~100):(1~10):(1~10):(1~10):(1~10):(1~10):(0.1~5):(0.1~10):(0.1~5):(0.1~5).

3. The method according to claim 1, wherein the mass ratio of inulin, ARILLUS *DIMOCARPUS LONGAN*, FRUCTUS *ZIZIPHUS JUJUBE*, FRUCTUS *LYCIUM BARBARUM*, RADIX *REHMANNIA GLUTINOSA* PRAEPARATA, SEMEN *JUGLANS REGIA*, HERBA *CISTANCHE TUBULOSA*, taurine, FRUCTUS *SCHISANDRA CHINENSIS* and CORTEX *CINNAMOMUM CASSIA* is 10:3:3:2:2:2:1:0.3:0.5:0.5.

4. The method according to claim 1, wherein the mass ratio of inulin, ARILLUS *DIMOCARPUS LONGAN*, FRUCTUS *ZIZIPHUS JUJUBE*, FRUCTUS *LYCIUM BARBARUM*, RADIX *REHMANNIA GLUTINOSA* PRAEPARATA, SEMEN *JUGLANS REGIA*, HERBA *CISTANCHE TUBULOSA*, taurine, FRUCTUS *SCHISANDRA CHINENSIS* and CORTEX *CINNAMOMUM CASSIA* is 50:2.5:5:2.5:6.25:3.75:0.75:0.25:2.5:2.5.

5. The method according to claim 1, the mass ratio of inulin, ARILLUS *DIMOCARPUS LONGAN*, FRUCTUS *ZIZIPHUS JUJUBE*, FRUCTUS *LYCIUM BARBARUM*, RADIX *REHMANNIA GLUTINOSA* PRAEPARATA, SEMEN *JUGLANS REGIA*, HERBA *CISTANCHE TUBULOSA*, taurine, FRUCTUS *SCHISANDRA CHINENSIS* and CORTEX *CINNAMOMUM CASSIA* is 20:2.5:1:4:1:4:1.5:5:1:0.1.

6. The method according to claim 1, wherein the powder formulation is in the form of a health food.

\* \* \* \* \*